United States Patent
Kim et al.

(10) Patent No.: US 6,954,557 B2
(45) Date of Patent: Oct. 11, 2005

(54) FOOT MEASUREMENT SYSTEM AND METHOD

(75) Inventors: Yong Jin Kim, Choongchungnam-do (KR); Si Kyung Kim, Daejun (KR); Hee Man Lee, Daejon (KR)

(73) Assignee: Leste Co., Ltd., Gongju-Si (KR)

( * ) Notice: Subject to any disclaimer, the term of this patent is extended or adjusted under 35 U.S.C. 154(b) by 697 days.

(21) Appl. No.: 09/956,960

(22) Filed: Sep. 21, 2001

(65) Prior Publication Data

US 2002/0048392 A1 Apr. 25, 2002

(30) Foreign Application Priority Data

Sep. 21, 2000  (KR) ........................................ 2000-55577

(51) Int. Cl.⁷ ................................................ G06K 9/36
(52) U.S. Cl. ...................... 382/286; 382/103; 382/128; 382/154; 356/600
(58) Field of Search ................................ 382/103, 128, 382/154, 282, 286, 291, 285, 289; 256/600, 611, 620, 622; 356/600, 614, 625

(56) References Cited

U.S. PATENT DOCUMENTS

| | | | | |
|---|---|---|---|---|
| 4,745,290 A | * | 5/1988 | Frankel et al. .......... 250/559.17 |
| 5,206,804 A | * | 4/1993 | Thies et al. .................... 705/27 |
| 5,339,252 A | * | 8/1994 | White et al. ................... 700/98 |
| 5,477,371 A | * | 12/1995 | Shafir .......................... 359/201 |
| 5,661,864 A | * | 9/1997 | Valiant et al. ............ 12/133 R |
| 6,006,412 A | * | 12/1999 | Bergmann et al. ....... 29/407.04 |

* cited by examiner

*Primary Examiner*—Bhavesh M. Mehta
*Assistant Examiner*—Yosef Kassa
(74) *Attorney, Agent, or Firm*—Staas & Halsey LLP (57) ABSTRACT

There are disclosed foot measurement systems and methods to scan someone's foot from the bottom and/or oblique topside directions for generating pixel data for the foot shape, and then to calculate and obtain main foot-dimensions and other information required for last design (for example, shoes design) using the generated pixel data. The foot measurement system comprises foot data generating means for generating pixel data for foot shape and transmitting them to the exterior, the pixel data being obtained by emitting light to a foot placed on a substrate and analyzing information of the reflected light; and image treatment means for generating foot image through analyzing the pixel data transmitted from the foot data generating means with line-scan algorithm and/or stereo vision algorithm.

4 Claims, 5 Drawing Sheets

FOOT MEASUREMENT SYSTEM AND METHOD

CROSS-REFERENCE TO RELATED APPLICATIONS

This application claims the benefit of Korean Patent Application No. 2000-55577 filed on Sep. 21, 2000, in the Korean Industrial Property Office, the disclosure of which is incorporated herein by reference.

BACKGROUND OF THE INVENTION

1. Field of the Invention

The present invention relates to foot measurement systems and methods; and, more particularly, to foot measurement systems and methods to scan someone's foot from the bottom and/or oblique topside directions for generating pixel data for the foot shape, and then to calculate and obtain main foot-dimensions and other information required for last design (for example, shoes design) using the generated pixel data.

2. Description of the Related Art

Generally, there has been known a method for fabrication of shoes or appliances for foot-remedy, in which molds for human feet are made using plaster bandages and the shoes or appliances for foot-remedy are fabricated using the molds with synthetic resins having suitable properties. In a case of fabricating general shoes made to order, a shoes maker draws the bottom outline of orderer's foot in a condition of putting the orderer's foot on a sheet of paper and measures the main sizes for the foot with a ruler. Such tasks are required for extraction of orderer's foot shape. The shoes maker then makes a foot framework fixed to the measured foot sizes to fabricate shoes with using the foot framework.

However, there are some shortcomings in the fabrication of mold by the plaster bandage and the fabrication of the foot-remedy shoes or appliances based on the mold. Namely, it takes a long time for performing the task, which does not allow mass production and may allow only individual fabrication for a particular person so that other persons cannot use the fabricated foot-remedy appliances. Furthermore, in the case of using the touch type foot-dimension's measurement method, the person to be measured should maintain an immobile posture for a long time, otherwise precise measurement cannot be obtained. In spite of the inconvenience, the measured data are not reproducible.

The fabrication of general shoes made to order also has inconveniences that the shoes maker measures orderer's foot sizes manually and that it takes a long time for the measurement. In spite of the inconveniences, the measurement cannot be precise so that the shoes maker cannot make the most suitable shoes to orderer's feet.

SUMMARY OF THE INVENTION

It is, therefore, an object of the present invention to provide foot measurement systems and methods to scan someone's foot from the bottom and/or oblique topside directions for generating pixel data for the foot shape, and then to calculate and obtain main foot-dimensions and other information required for last design (for example, shoes design) using the generated pixel data.

In accordance with an embodiment of the present invention, there is provided a foot measurement system comprising: foot data generating means for generating pixel data for foot shape and transmitting them to the exterior, said pixel data being obtained by emitting light to a foot placed on a substrate and analyzing information of the reflected light; and image treatment means for generating foot image through analyzing said pixel data transmitted from said foot data generating means with line-scan algorithm and/or stereo vision algorithm.

Wherein it is preferred that said foot data generating means comprises: an image generating part for generating said pixel data for foot shape through emitting light to said foot and analyzing said information of the reflected light; a foot data memory part for storing said generated pixel data; driving means for moving said image generating part; and a control part for controlling said image generating part, said foot data memory part and said driving part.

Said image generating part may comprise a light generating part (light source) below said substrate, for emitting light to the bottom of said measured foot; and an image sensor or sensors for detecting the light reflected from the bottom of said foot and generating said pixel data, and said driving means may be for moving said image generating part horizontally below said substrate. Said image generating part may also comprise a light generating part obliquely placed over said measured foot, for obliquely emitting light to the top and side surfaces of foot; and an image sensor or sensors for detecting the light reflected from the surface of foot and generating said pixel data, and said driving means may be for rotating said image generating part around said measured foot.

In accordance with another embodiment of the present invention, there is provided a foot measurement method comprising the steps of: emitting light to the bottom of foot and/or the top and side surface of foot and detecting the reflected light with a sensor or sensors; converting said reflected light detected with said sensor(s) into electronic signal and converting said electronic signal into pixel data including image information; generating three-dimensional image coordinates of foot from said pixel data with using a line scan method and/or a stereo vision method; and calculating at least one distance and coordinates for each part of foot from said three-dimensional image coordinates.

BRIEF DESCRIPTION OF THE DRAWINGS

The above and other objects and features of the present invention will become apparent from the following description of preferred embodiments given in conjunction with the accompanying drawings, in which.

DETAILED DESCRIPTION OF THE PREFERRED EMBODIMENTS

The invention will be illustrated in detail by the following preferred embodiments with reference to the accompanying drawings. The embodiments below will explain line-scan manner to generate information for the bottom of foot by scanning the bottom of foot and stereo vision manner to generate information for the three-dimensional shape of top and side surface of foot by scanning the top and side surface of foot with laser line generator. However, the above-mentioned embodiments could be changed and modified by a person having ordinary skill in the art to which the invention pertains. Therefore, the idea and scope of the invention is not limited to the specific line-scan and stereo-vision manners described below, and might include the changes and modifications.

Figure 1:
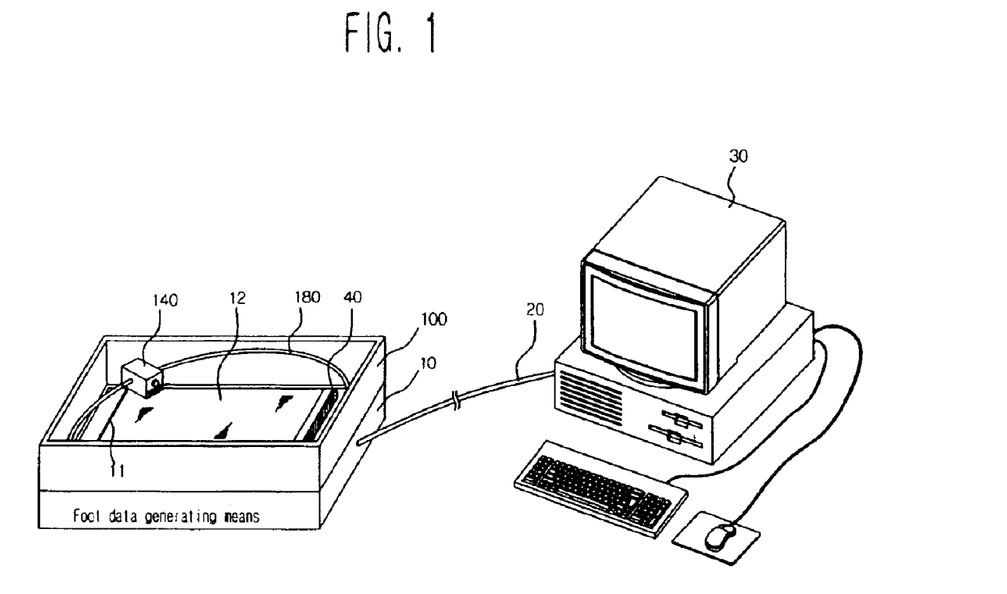
FIG. 1 shows a device configuration for depicting a foot measurement system according to an embodiment of the present invention.
Figure 2:
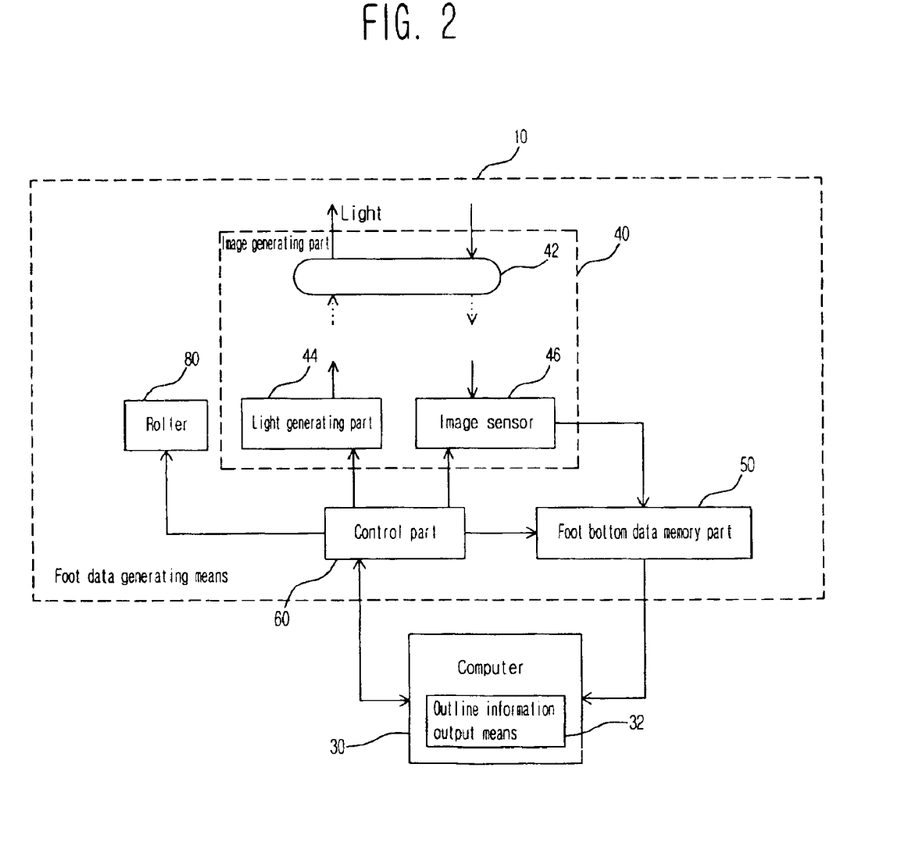
FIG. 2 is a block diagram for depicting the configuration of a first foot data generating means for generating data for the bottom shape of foot with line-scan manner, in the foot measurement system according to an embodiment of the present invention depicted in FIG. 1.
Figure 3:
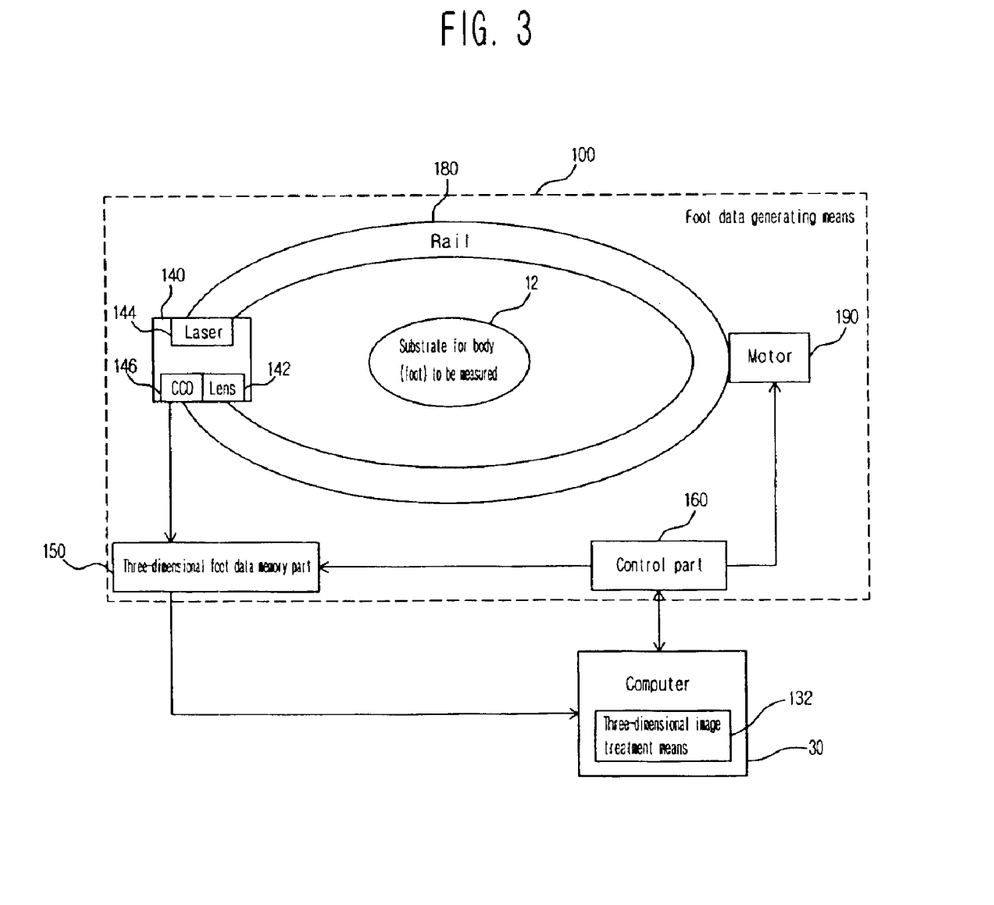
FIG. 3 is a block diagram for depicting the configuration of a second foot data generating means for generating data for the three-dimensional shape of the top and side surface of foot with stereo vision manner, in the foot measurement system according to an embodiment of the present invention depicted in FIG. 1.

FIG. 1 shows a device configuration for depicting a foot measurement system according to an embodiment of the present invention. FIG. 2 is a block diagram for depicting the configuration of a first foot data generating means for generating data for the bottom shape of foot with line-scan manner, in the foot measurement system according to an embodiment of the present invention depicted in FIG. 1. FIG. 3 is a block diagram for depicting the configuration of a second foot data generating means for generating data for the three-dimensional shape of the top and side surface of foot with stereo vision manner, in the foot measurement system according to an embodiment of the present invention depicted in FIG. 1.

As shown in FIG. 1, the foot measurement system according to the invention may include a first foot data generating means 10, a second foot data generating means 100, interface cable 20, and a computer 30. The computer 30 is to transmit an instructions signal of foot measurement via the interface cable 20 to the first and second foot data generating means 10 and 100 according to operation of a shoes maker, to receive pixel data for the bottom of foot and the three-dimensional shape of the top and side surface of foot generated from the first and second foot data generating means 10 and 100, and then to generate information for the shape of foot using the transmitted pixel data for providing the shoes maker or designer with it.

The first foot data generating means 10 may emit light from a light source under a substrate, preferably, a glass substrate 12 formed for that a person to be measured places his or her foot on it to measure the shape of foot. The first foot data generating means 10 may then generate pixel data for the bottom of foot from the reflected light to transmit the pixel data via the interface cable 20 to the external. On the glass substrate 12 is formed an end line 11, which can be used for matching the heel of the person to be measured to it when the person to be measured places his or her foot on the glass substrate 12. When the end line 11 is detected with the light emitted from a bottom image generating part 40, the first foot data generating means 10 becomes to terminate the generation of pixel data for the bottom of foot.

Referred to FIG. 2, the first foot data generating means 10 may include the bottom image generating part 40, a foot bottom data memory part 50, a control part or control unit 60, a roller driving part (not shown), and a roller 80. The bottom image generating part 40 comprises a lens 42, a light source or light generating part 44 and an image sensor 46.

The bottom image generating part 40 may emit light from the light source or light generating part 44 under the glass substrate 12 to the foot placed on the substrate 12, and detect the light reflected from the substrate 12 with the image sensor 46 to generate the pixel data for the bottom of foot. The light source or light generating part 44 may be allowed to emit white light or mixed light of Red (R), Green (G) and Blue (B) light to the bottom of the glass substrate 12. The image sensor 46 can then collect the light reflected from the glass substrate 12, through the lens 42. The collected light is converted into electronic signal, and which is then converted into digital signal, the pixel data for the bottom of foot. Therefore, the image sensor 46 may include an A/D converter. The foot bottom data memory part 50 can store the pixel data for the bottom of foot transmitted from the image sensor 46, according to the control signal inputted from the control part 60, and transmit the stored pixel data into the computer 30 according to the instruction of the control part 60.

The control part 60 can also output roller-driving signal for driving the roller 80 in response to the instructions signal for the measurement of foot shape transmitted via the interface cable 20 from the computer 30. The roller 80 can then move the image generating part 40 along to the direction of the end line 11 in response to the roller-driving signal inputted from the control part 60.

The second foot data generating means 100 may emit laser line to the top and side surface of foot, and detect the light reflected from the foot to be measured, thereby generating pixel data for the top and side surface of foot. Referred to FIGS. 2 and 3, the second foot data generating means 100 may include a three-dimensional image generating part 140, a three-dimensional foot data memory part 150, a control part or control unit 160, a CCD cart-movable rail 180, and a CCD cart-driving motor 190. The three-dimensional image generating part 140 may comprise a light source or light generating part 144 such as a laser line generator, a lens 142, and a CCD image sensor 146. Here, each of the control part 160 and the three-dimensional foot data memory part 150 may be integrated with the control part 60 and the foot bottom data memory part 50, respectively, or they may be formed separately.

The light generating part 144 performs the function of laser line generator, which emits laser line to the top and side surface of foot to be measured. The CCD image sensor 146 may collect and capture the light reflected from the top and side surface of foot, through the lens 42. The collected laser line may be then converted into electronic signal, and which may be converted into digital signal, the three-dimensional pixel data for the top and side surface of foot. Therefore, the image sensor 146 may include an A/D converter.

The three-dimensional foot data memory part 150 can store the information for the laser line position, namely the three-dimensional data for foot transmitted from the CCD image sensor 146 according to the control signal inputted from the control part 160 by the operation of computer 30, and transmit the stored three-dimensional data for foot into the computer 30.

The control part 160 may output a signal for driving the stepping motor 190 in response to the instructions signal for the measurement of three-dimensional foot shape transmitted from the computer 30, so that the three-dimensional image generating part 140 can be moved 360 along the clockwise or counter clockwise direction on the CCD cart-movable rail 180, which is placed on the circumference of the foot to be measured. It is preferred that the three-dimensional image generating part 140 should be moved 360 on the CCD cart-movable rail 180 to be returned to the original position. It is also preferred that the CCD cart-movable rail 180 and the three-dimensional image generating part 140 work together with a three-dimensional measurement software for the treatment of foot image. It is also preferred that the foot image measurement start time and end time of the image generating part 140 are synchronized with the rotating time of the rail 180.

The computer 30 may receive the pixel data from the foot bottom data memory part 50 and/or the three-dimensional foot data memory part 150, and perform the function as means for treating the line-scan and/or stereo-vision image to extract main foot dimensions. As shown in FIGS. 2 and 3, the computer 30 may include outline information output means 32 and/or image treatment means 132, which can take the pixel data for the bottom of foot during the bottom image generating part 40 are moving linearly, and/or the three-dimensional image data stored during the three-dimensional line image generating part 140 is rotating 360 along the clockwise or counter-clockwise, and perform the reconstruction and rendering of them into the image information for the bottom of foot and/or the top and side surface of foot. The three-dimensional image treatment means 132 depicted in FIG. 3 may be integrated with the outline information output means 32 depicted in FIG. 2, or be formed separately.

Figure 4:
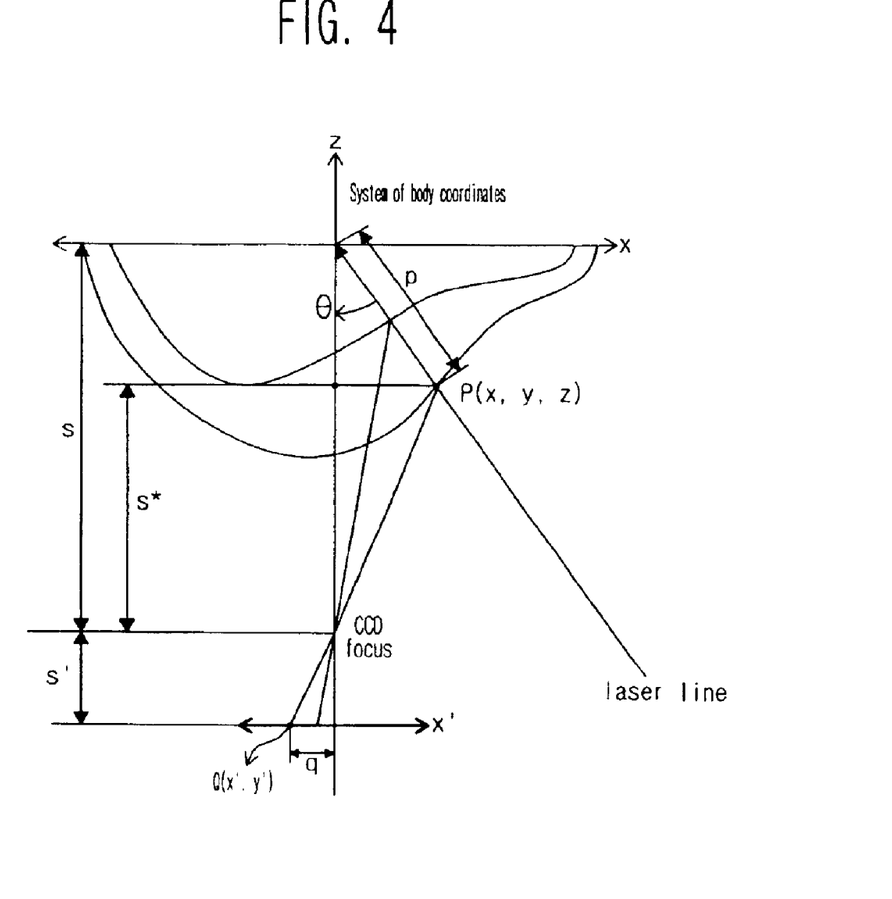
FIG. 4 is a drawing for describing a method for calculating foot shape information from the pixel data, in the foot measurement system according to an embodiment of the present invention.

Next, with referring to FIG. 4 will be illustrated an embodiment of method for calculating the image information of foot from the three-dimensional pixel data generated by the second foot data generating means 100. FIG. 4 is a drawing for describing the use of optical triangle method as an example of principle for three-dimensional measurement. The optical triangle method is a technique for displacement measurement based on the principle of geometrical optics. A coordinate system of the optical triangle method exists within a plane, and two of optical axes are intersected with an angle of $\theta$ to the coordinate axis of z. In the principle for the measurement of three-dimensional shape using the optical triangle method applied to the invention, one of the two optical axes is a laser line for forming an optical point on the surface of a body to be measured, and the other is an optical axis of CCD image for collecting the light of image on the optical point. The optical point formed on the body to be measured becomes to move linearly along the laser line according to the relative position of the body to be measured. The optical point is projected on the image coordinates [$\alpha$ (width)×$\beta$ (length)] of CCD array plane. The CCD then converts the intensity of light into electronic signal, and which is then converted into computer monitor coordinates [N (width)×M (length)] by image grabber. The computer monitor coordinates is extracted to be converted into image coordinates Q (x',y') of CCD array to calculate the distance S* from the body to be measured to the CCD with applying the optical triangle method. In order to obtain the tree-dimensional shape of the body to be measured, the CCD rotates 360 with a distance to the body along the circumference of the body, and measures the distance from the body to the CCD at a predetermined rotating angle. After that, the optical point is converted into body coordinates P (x,y,z), which have the center of the body to be measured as the origin of the coordinates.

Now, a more detailed description will be provided with referring to FIG. 4. The light at a certain point P(x,y,z) of the coordinates of the body is projected on the CCD array image coordinates Q(x',y'). The image coordinates become to move along the system of image coordinates x' according to the change of distance from the body to be measured to the CCD. When the focus distance of CCD lens is defined to f, the relation of given body distance s and the image distance s' is obtained by paraxial optics as the following mathematical formula (1).

$$\frac{1}{s'} = \frac{1}{f} - \frac{1}{s} \text{ or } s' = \frac{s \times f}{(s-f)} \quad (1)$$

The body distance s* from the CCD for a certain point P on the surface of the body is obtained from the geometric relation as the following formula (2).

$$s^* = s - p \cos \theta \quad (2)$$

Here, p is a distance from the origin of the coordinates for the point P of the body. The distance q from the origin of the image coordinate system for the image coordinates Q is defined as in the following formula (3) based on the magnification relation of CCD lens.

$$\frac{q}{p \times \sin\theta} = \frac{s'}{s^*} \quad (3)$$

When the formula (2) is substituted into the formula (3), the relation between the distance p of the laser optical point moved on the track of body and the distance q of the image coordinates corresponded to the distance p is obtained as the following formula (4).

$$p = \frac{q \times s}{(s' \times \sin\theta) + (q \times \cos\theta)} \quad (4)$$

Here, the obtained p is a distance from the origin in the coordinate system of the body to the laser optical point emitted on the surface of body. The coordinate P(x,y,z) of the body may be obtained using this value. When the CCD cart rotates to an angle of $\phi$ along the circumference of the body to be measured by the operation of stepping motor, the body coordinate P(x,y,z) obtained by the formula (4) rotates to the angle of $\phi$. Therefore, the model coordinates $P_M(x_m, y_m, z_m)$ may be generated by compensating the coordinates with the rotated angle ($\phi$) in the use of the formula (5).

$$\begin{bmatrix} x_m \\ y_m \\ z_m \end{bmatrix} = \begin{bmatrix} \cos\varphi & 0 & -\sin\varphi \\ 0 & 1 & 0 \\ \sin\varphi & 0 & \cos\varphi \end{bmatrix} \begin{bmatrix} x \\ y \\ z \end{bmatrix} \quad (5)$$

Examples for the information of foot calculated by the outline information input means 32 and image treatment means 132 using the pixel data for the bottom of foot and the three-dimensional image of foot may include the followings: Ball Girth; Foot Length, which is a distance from the end point of foot (heel) to the longest toe end; Instep Length, which is a distance from the end point of foot to the inside middle foot point; Fibular Instep Length, which is a distance from the end point of foot to the outside middle foot point; Anterior Foot Length, which is a distance from the longest toe end to the inside middle foot point; Foot Breadth, which is a distance from the inside middle foot point to the outside middle foot point; Heel Breadth, which is a vertical distance to Foot Length on the location distant to the degree of 16% of Foot Length from the end point of foot; Ball Breadth, which is a vertical distance to Foot Length from the inside middle foot point to the outside middle foot point, namely, is a vertical component of Foot Breadth to Foot Length; Ball Flex Angle, which is a foot boundary angle made by the fore and rear parts of foot at a time of walking; Medial Angle, which is a foot boundary angle distinct and made by the anatomical fore and rear parts of foot; Lateral Angle, which is an angle formed between the side of foot and the centerline of foot; Toe V Angel, which is an angle formed between the little toe and the centerline of foot; Toe I Angle, which is an angle formed between the big toe and the centerline of foot; and Little Toe Angle.

A serial port is equipped in the first and second foot data generating means 10 and 100 of the foot measurement system according to the invention, in order to perform communication with the computer 30. The interface cable 20, which is a serial port cable, is connected between the serial port and the computer 30. Therefore, when a shoes maker inputs instructions signal for the measurement of three-dimensional foot shape through the computer 30, the signal to start the measurement of foot shape may be transmitted to the first and second foot data generating means 10 and 100 through the interface cable 20, and the light generating parts 44 and 144 may then be driven to emit light mixed with R, G and B and line laser light onto the surface of foot placed on the substrate 12. The light and laser line projected onto the foot is captured by the image sensors 46 and 146, and are converted into electronic signals including the image information for the shape of foot, which are stored in the foot data memory parts 50 and 150. The image information for the shape of foot may then be transmitted to the computer 30 and immediately converted into the final foot information required for the fabrication of shoes and the like. Therefore, the foot measure system according to the invention can measure the foot shape of a person to be measured and provide design data useful to last designers for the fabrication of shoes.

Figure 5:
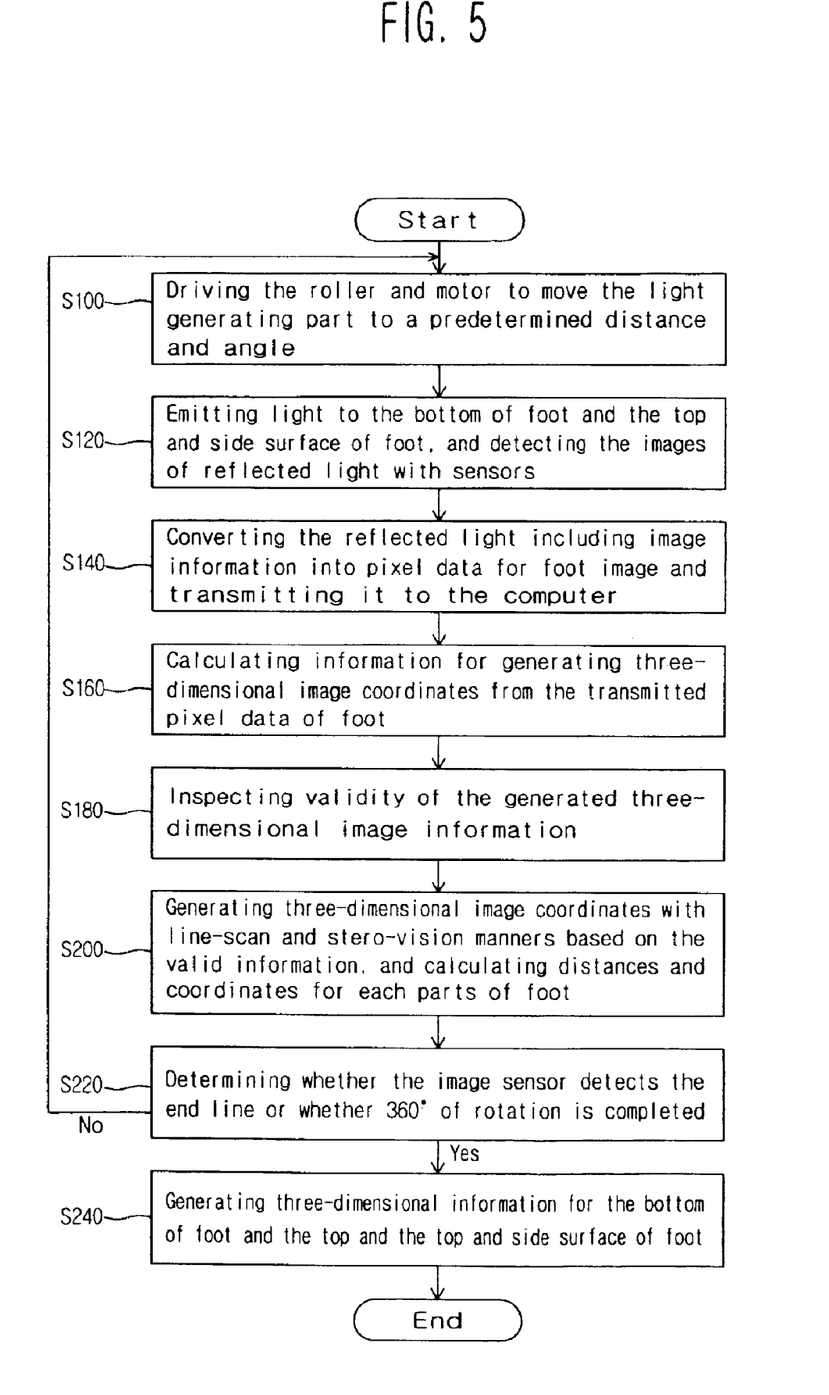
FIG. 5 is a flow chart for describing the operation of a foot measurement method according to an embodiment of the present invention.

FIG. 5 is a flow chart for describing the operation of a foot measurement method according to an embodiment of the present invention.

As shown in FIG. 5, first, a foot to be measured is placed on the substrate 12 of the first and second foot data generating means 10 and 100, and instructions signal for the measurement of foot shape is transmitted from the computer 30 to the control parts 60 and 160. The control parts 60 and 160 then drive the roller 80 and the motor 190 to move the light generating parts 44 and 144 to a predetermined distance and angle (S100).

At this time, the light generating parts 44 and 144 emit light to the bottom of foot and the top and side surface of foot, respectively, and the image sensors 46 and 146 detect the images of light reflected through the lenses 42 and 142, respectively (S120). Briefly, the image generating parts 10 and 100 emit laser line light on the foot to be measured at each of predetermined distances and angles, collect the reflected light through the lenses 32 and 142, and detect the collected light with the sensors 46 and 146 such as CCD array. The lights projected to the sensors 46 and 146 are converted into electronic signals, which are converted into pixel data of foot by image grabber, and which are transmitted to the computer 30 via the interface cable 20 connecting the image generating parts 10 and 100 to the computer 30 (S140).

Then, the outline information output means 30 and the image treatment means 132 embedded in the computer 30 calculates the information for generating three-dimensional image coordinates for foot with using the pixel data for the three-dimensional image of foot transmitted via the interface cable 20 (S160). The three-dimensional image information generated by this procedure is inspected of whether it is valid or not (S180). The validity for the information is determined based on the expected distance from the foot to be measured. At this time, invalid information is discarded and only valid information is taken.

Next, three-dimensional image coordinates are generated with the line-scan method and/or stereo-vision method using the valid information to calculate distances and coordinates for each parts of foot (S200). At this time, it is preferred that the information for the entire foot shape should be produced from a specific number of obtained valid values in the use of interpolation. It is also preferred that a model table consisted of the information for facets to construct a three-dimensional shape of foot and attribute values for the facets should be made using each of the obtained information.

After the coordinates and distances for each parts of foot are calculated, the motor 190 and the roller 80 are driven to determine whether the end line is detected by the image sensor 46 and the image sensor 146 is rotated 360 along the rail 180, and to perform the procedure for obtaining data for the next locations repeatedly (S220). When all of the information for the bottom surface and the top and side surface of foot are collected during such a procedure, the outline information output means 32 and the three-dimensional treatment means 132 generate the three-dimensional information for the bottom of foot and the top and side surface of foot so as to be used as data for a foot shape in last design (s240).

In the above, there is described a method for measuring a foot shape, in which after data is obtained at a certain location of the specific sensors 46 and 146, the foot shape is calculated and then the locations of sensors 46 and 146 move to the next location. However, after all of data are obtained at all of the locations of sensors 46 and 146, the foot shape may be calculated to obtain the required information.

As described above, the present invention is to solve the shortcomings in the prior art that the person to be measured should be maintained at an unnatural state of immobile posture for a long time in order to perform a measurement of foot shape and that the data obtained by the measurement are not reproducible. Further, the present invention can obtain three-dimensional data for a foot shape within a short time by using a computer.

The present invention relates to a three dimensional foot shape measurement system, which is processed by a method for emitting laser line to the foot to be measured, or emitting R, G and B LED, and a method for driving a image CCD using stereo-vision manner in order to measure three-dimensional data for foot for a short time. Therefore, the present invention is economically profitable in the view of facility for transportation and treatment of the foot measurement system, and in the view of the prices of the sensors.

The present invention can also obtain within a short time, the data such as Ball Girth, Ball Breadth, Ball Flex Angle, Medial Angle, Lateral Angle, Toe V Angle, and Toe I Angle, which cannot be obtained by the contact type of measurement system or device used in the prior art.

The present invention can also conveniently measure foot sizes and three-dimensional foot image data of any customers by equipping the measurement system according to the present invention in a store, and provide shoes suitable to the customers by making the shoes in the use of the measured foot shape data.

While the present invention has been described with respect to a certain preferred embodiment only, other modifications and variations may be made without departing from the spirit and scope of the present invention as set forth in the following claims.

What is claimed is:

1. A foot measurement system comprising:
   foot data generating means for generating pixel data for foot shape and transmitting them to the exterior, said pixel data being obtained by emitting light to a foot place on a substrate and analyzing information of the reflected light; and image treatment means for generating a foot image through analyzing said pixel data transmitted from said foot data generating means with line-scan algorithm and/or stereo vision algorithm, wherein said foot data generating means comprises:
an image generating part for generating said pixel data for said foot shape through emitting light to said foot and analyzing said information of the reflected light,
a foot data memory part for storing said generated pixel data,
driving means for moving said image generating part, and
a control part for controlling said image generation part, said foot data memory part and said driving part; and wherein said image generating part comprises a light generating part obliquely placed over said measured foot, for obliquely emitting light to the top and side surface of said foot; and an image sensor or sensors for detecting the light reflected from the surface of said foot and generating said pixel data, and said driving means is for rotating said image generating part around said measured foot.

2. The foot measurement system according to claim 1, wherein over said substrate is equipped a circular type of movement rail on which said image generating part can be mounted to rotate around said measured foot.

3. The foot measurement system according to claim 1, wherein said image generating part further comprises a lens or lenses in the front of said image sensor(s), for collecting said reflected light.

4. The foot measurement system according to claim 1, wherein said image treatment means extracts from said pixel data transmitted from said foot data generating means, at least one piece of information selected from the group consisting of the following data:

Ball Girth;

Foot Length, which is a distance from the end point of foot to the longest to end;

Instep Length, which is a distance from the end point of foot to the inside middle foot point;

Fibular Instep Length, which is a distance from the end point of foot to the outside middle foot point;

Anterior Foot Length, which is a distance from the longest toe end to the inside middle foot point;

Foot Breadth, which is a distance from the inside middle foot point to the outside middle foot point;

Heel Breadth, which is a vertical distance to Foot Length on the location distant to the degree of 16% of Foot Length from the end point of foot;

Ball Breadth, which is a vertical distance to Foot Length from the inside middle foot point to the outside middle foot point, namely, is a vertical component of Foot Breadth to Foot Length;

Ball Flex Angle, which is a foot boundary angle made by the fore and rear parts of foot at a time of walking;

Medial Angle, which is a foot boundary angle distinct and made by the anatomical fore and rear parts of foot;

Lateral Angle, which is an angle formed between the side of foot and the centerline of foot;

Toe V Angel, which is an angle formed between the little toe and the centerline of foot;

Toe I Angle, which is an angle formed between the big toe and the centerline of foot; and Little Toe Angle.

* * * * *